United States Patent [19]

Krepski et al.

[11] Patent Number: 5,194,623
[45] Date of Patent: Mar. 16, 1993

[54] AZLACTONE BASED PHOTOGRAPHIC REAGENTS

[75] Inventors: Larry R. Krepski, White Bear Lake; Sharon M. Simpson, Lake Elmo, both of Minn.

[73] Assignee: Minnesota Mining and Manufacturing Company, St. Paul, Minn.

[21] Appl. No.: 575,835

[22] Filed: Aug. 31, 1990

[51] Int. Cl.$^5$ ............... C07D 249/18; C07D 249/04; C07D 257/04; C07D 235/28; C07D 233/00
[52] U.S. Cl. ............... 548/261; 548/251; 548/253; 548/255; 548/309.7; 548/304.4; 548/338.1; 548/345.1; 544/235
[58] Field of Search ............... 548/253, 261, 305, 255, 548/251, 312

[56] References Cited

U.S. PATENT DOCUMENTS

| | | | |
|---|---|---|---|
| 4,137,079 | 1/1979 | Houle | 96/55 |
| 4,138,265 | 2/1979 | Shiao | 96/114.1 |
| 4,245,033 | 1/1981 | Eida et al. | 430/353 |
| 4,378,424 | 3/1983 | Altland et al. | 430/352 |
| 4,451,561 | 5/1984 | Hirabayashi et al. | 430/619 |
| 4,837,141 | 6/1989 | Kohno et al. | 430/559 |

OTHER PUBLICATIONS

Research Disclosure 16977, "Antifoggants in certain photographic and photothermographic materials".

*Primary Examiner*—David B. Springer
*Attorney, Agent, or Firm*—Gary L. Griswold; Walter N. Kirn; Mark A. Litman

[57] ABSTRACT

Novel compounds derived from azlactones act as precursors for photographically active groups. The active groups are released at an appropriate time in the use of photographic and photothermographic systems.

15 Claims, No Drawings

AZLACTONE BASED PHOTOGRAPHIC REAGENTS

FIELD OF THE INVENTION

This invention relates to novel omega-substituted-2-propioamidoacetyl and omega-substituted-3-propioamidopropionyl compositions and to methods of preparation thereof. The novel compositions are useful as photographic reagents.

BACKGROUND INFORMATION

Photographic elements are generally composed of many different materials, both photosensitive and non-photosensitive materials, coated in multiple layers. The number of layers can be considerable, especially in color imaging, with each primary color forming material present in a layer that is separated from other layers by barrier layers. In addition to the photosensitive materials such as various silver salts and leuco dye reagents, it has been found advantageous to add various other reagents that perform functions such as filtering, sensitization, development inhibition or acceleration, antihalation or antifogging, toning, image stabilization, or preservation of the imaging material during storage. It is often desirable to add a particular photographically useful reagent to a particular layer of the imaging construction, and it is usually important that the reagent not sublime or migrate into an adjoining layer prematurely. Unfortunately, it is often found that when different photographically useful reagents are added to imaging materials, they do react with each other during storage of the imaging materials prior to processing, or decompose by the action of heat or oxygen. Thus these reagents do not exhibit the enhanced performance effects that were expected. Additionally, many reagents that exhibit a desirable effect such as stabilization of an image after processing are found to have a deleterious effect on the initial sensitometric characteristics of the imaging material.

As a means of addressing these problems, reactive photographically useful reagents have been blocked with various modifying groups. These blocking or modifying groups convert the reactive photographically useful reagent into a form that is more stable, or inert, or less migratable or diffusible. However, these blocking or modifying groups are generally designed such that they are removed from the photographically useful reagent at some stage of processing which may, for example, involve heating or treatment with alkali. Thus, the blocked or protected photographically useful reagent is actually a precursor reagent from which the photographically useful reagent is liberated at some point during processing.

Various blocking techniques have been utilized. U.S. Pat. No. 3,615,617 describes acyl blocked photographically useful reagents. U.S. Pat. Nos. 3,674,478 and 3,993,661 describe hydroxyarylmethyl blocking groups. Thiocarbonate blocking groups are described in U.S. Pat. No. 3,791,830, and thioether blocking groups in U.S. Pat. Nos. 4,335,200, 4,416,977 and 4,420,554. useful reagents which are blocked as urea or thiourea derivatives are described in U.S. Pat. No. 4,310,612. Blocked imidomethyl derivatives are described in U.S. Pat. No. 4,350,752, and imide or thioimide derivatives are described in U.S. Pat. No. 4,888,268. Removal of all of these aforementioned blocking groups from the photographically useful reagents is accomplished by an increase of pH during alkaline processing conditions of the exposed imaging material.

Other blocking groups which are thermally sensitive have also been utilized. These blocking groups are removed by heating the imaging material during processing. Photographically useful reagents blocked as thermally-sensitive carbamate derivatives are described in U.S. Pat. Nos. 3,844,797 and 4,144,072. These carbamate derivatives presumably regenerate the photographic reagent through loss of an isocyanate. Hydroxymethyl blocked photographic reagents which are unblocked through loss of formaldehyde during heating are described in U.S. Pat. No. 4,510,236. Photographic reagents which are blocked by a Michael-type addition to the carbon-carbon double bond of either acrylonitrile or alkyl acrylates are described in U.S. Pat. Nos. 4,009,029 and 4,511,644, respectively. Heating of these blocked derivatives causes unblocking by a retro-Michael reaction.

Various disadvantages attend these different blocking techniques. Highly basic solutions which are necessary to cause deblocking of the alkali sensitive blocked derivatives are corrosive and irritating to the skin. With the photographic reagents which are blocked with a heat removable group, it is often found that the liberated reagent or by-product, for example, acrylonitrile, can react with other components of the imaging construction and cause adverse effects.

SUMMARY OF THE INVENTION

Briefly, this invention provides novel precursors to photographically useful reagents which are completely stable under storage conditions of photographic materials and appear to release the photographically useful reagent at a desired time by heating during processing. These novel precursors to photographically useful reagents are represented by the following general Formula I:

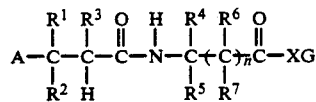

wherein A represents a residue of a photographically useful reagent in which a hydrogen atom of the photographically useful reagent has been replaced by the remainder of the structure shown in general Formula I;
n is 0 or 1;
X represents an oxygen, nitrogen or sulfur atom; and
G represents an organic group, preferably a ballasting group.
In this application:
"alkenyl" and "alkenylene" mean the monovalent and polyvalent residues remaining after removal of one and at least two hydrogen atoms, respectively, from an alkene containing 2 to 20 carbon atoms; functional groups which may be present are one or more aryl, amide, thioamide, ester, thioester, ketone (to include oxo-carbons), thioketone, nitrile, nitro, sulfide, sulfoxide, sulfone, disulfide, tertiary amine, ether, urethane, dithiocarbamate, quaternary ammonium and phosphonium, halogen, silyl, silyloxy, and the like, wherein the functional groups requiring substituents are substituted with hydrogen, alkyl, or aryl groups where appropriate; additionally, the alkenyl and alkenylene residues may contain one or more catenary S, O, N, P, and Si heteroatoms;

"alkyl" and "alkylene" mean the monovalent and polyvalent residues remaining after removal of one and at least two hydrogen atoms, respectively, from a linear or branched chain hydrocarbon having 1 to 20 carbon atoms, functional groups and catenary heteroatoms which may be present are the same as those listed under the "alkenyl" definition;

"aryl" and "arylene" mean the monovalent and polyvalent residues remaining after removal of one and at least two hydrogen atoms, respectively, from an aromatic compound (single ring and multi- and fused-cyclic) having 5 to 12 ring atoms in which up to 5 ring atoms may be selected from S, Si, O, N, and P heteroatoms, functional groups which also may be present are the same as those listed under the "alkenyl" definition;

"azlactone" means 2-oxazolin-5-one groups of Formula II and 2-oxazin-6-one groups of Formula III

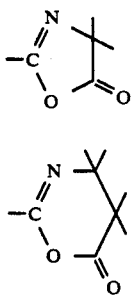

II

III

"cycloalkyl" and "cycloalkylene" mean the monovalent and polyvalent residues remaining after removal of one and at least two hydrogen atoms, espectively, from a cyclic hydrocarbon having 3 to 12 ring atoms of which one or more of the ring atoms may be N, O, S, P, and Si atoms and functional groups listed under the "alkenyl" definition may also be present;

"lower alkyl" means C-1 to C-4 alkyl;

"Michael reaction" means the catalyzed or uncatalyzed addition of a "Michael donor", illustrated by a nitrogen nucleophile (IV) in the equation below, to an alkenyl azlactone "Michael acceptor" (V) to form a "Michael adduct" reaction product (VI):

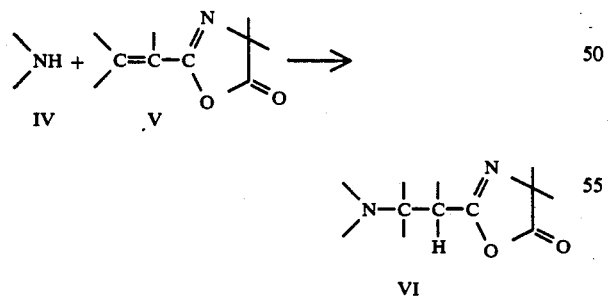

IV    V

VI

"Michael donor" means the nucleophilic reactant in a Michael reaction;

"Michael acceptor" means the electrophilic reactant in a Michael reaction;

"substantially perfluorinated" means hydrocarbon groups in which at least 50 percent, preferably at least 85 percent, and more preferably 100 percent, of the hydrogen atoms have been replaced by fluorine, and one or more heteroatoms of N, O, S, P, and Si may be present; and "azlactone ring opening reaction" means the catalyzed or uncatalyzed addition reaction of a nucleophile, HXG (wherein X=O, S, NH, or NR and R means independent selections of alkyl and/or aryl groups), as illustrated by an HXG nucleophile in the equation below, to an azlactone (11) to provide the α-amidoacetyl derivative (VII)

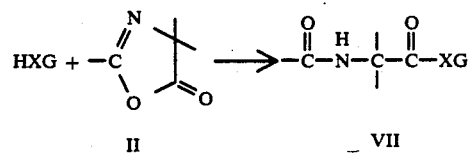

II    VII

DETAILED DESCRIPTION OF THE INVENTION

The present invention provides novel omega-substituted-2-propioamidoacetyl and omega-substituted-3-propioamidopropionyl compositions of general Formula I:

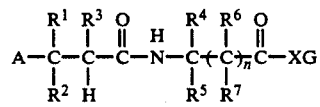

I wherein $R^1$, $R^2$ and $R^3$ are independently hydrogen or lower alkyl, with the proviso that $R^1$ can also represent an aryl group when $R^2$ and $R^3$ are hydrogen;

$R^4$ and $R^5$ independently represent an alkyl group of 1 to 14 carbon atoms, a cycloalkyl group of 3 to 12 carbon atoms, an aryl group of 5 to 12 ring atoms, or $R^1$ and $R^2$ taken together with the carbon atom to which they are joined form a carbocyclic ring of 4 to 12 ring atoms;

$R^6$ and $R^7$ independently are hydrogen or methyl;

n is 0 or 1;

X represents an oxygen, nitrogen or sulfur atom, or NH or NR and R means independent selections of alkyl and/or aryl groups;

G represents an organic group, including hydrogen, and can be alkyl or cycloalkyl, aryl or alkaryl, low molecular weight (one, in the case of G=H) or high (to essentially infinite molecular weight in the case of crosslinked polymers);

G can contain one or more of S, O, N, P, halogen, and Si atoms; and functional groups that can be included in G are one or more alkyl, alkenyl, aryl, amide, thioamide, ester, thioester, ketone (to include oxo-carbons), thioketone, nitrile, nitro, sulfide, sulfoxide, sulfone, disulfide, tertiary amine, ether, urethane, dithiocarbamate, quaternary ammonium and phosphonium, halogen, silyl, silyloxy, and the like, wherein the functional groups requiring substituents are substituted with hydrogen, alkyl, or aryl groups where appropriate; and A represents a residue of a Michael donor AH as described in our pending application entitled "Azlactone Michael Adducts," File No. 45053USA1A, incorporated herein by reference and AH is a photographically useful reagent such as a dye or leuco dye, filtering or sensitization agent, development inhibitor or accelerator, toner, antifoggant, stabilizer, color developing agent or color coupler.

In a preferred, narrow practice of the present invention, AH can be defined as a post-processing stabilizing reagent. This is a reagent, which when released from the propioamidoacetyl or propioamidopropionyl composition, stabilizes the image formed after processing.

In general Formula I, A represents the residue of a "primary" post-processing stabilizer, AH, in which the hydrogen atom has been replaced by the propioamidoacetyl or propioamidopropionyl group. The propioamidoacetyl or propiopropionyl group acts as a blocking group to block the activity of the primary stabilizer AH. If AH is left unblocked and added to the photographic emulsion at the same molar concentration as the composition of Formula I, AH desensitizes said emulsion. In addition to functioning as a blocking group for the "primary" stabilizer AH, the propioamidoacetyl or propioamidopropionyl functionality of the composition of Formula I has another utility, and that is to act as a "secondary" stabilizer for the image. The α-amidoacetyl composition of Formula X, below, act as "secondary" stabilizers. While not wishing to be bound by any particular mechanism or explanation for the observed stabilization effect of the composition of Formula I, it is possible that the combination of processing heat and photothermographic environment causes release of the "primary" stabilizer AH from the composition of Formula I through a retro-Michael reaction. If AH is liberated by this retro-Michael reaction, the "secondary" stabilizer, which is the composition of Formula X, would also be liberated. It is thus possible by the present invention to provide "secondary" stabilization of the image by a composition of Formula X which is generated in situ by the decomposition of the composition of Formula I.

Post-processing stabilizing groups usually have a sulfur or nitrogen atom available for complexing silver ion. The compounds are usually ring structures with the sulfur and/or nitrogen within the ring or external to the ring. These compounds are well known to the ordinarily skilled photographic chemist.

Suitable primary stabilizers are well known in the art such as nitrogen-containing substituted or unsubstituted heterocyclic rings; such as benzimidazole, benzotriazole; triazoles; tetrazoles; imidazoles; various mercapto-containing substituted or unsubstituted compounds; such as mercapto triazoles, mercepto tetrazoles; thio-substituted heterocycles; or any such compound that stabilizes the said emulsion but at such concentrations desensitizes the initial sensitometric response if left unblocked. Many of such compounds are summarized in Research Disclosure 29963 from March, 1989 entitled "Photothermographic Silver Halide Systems."

In addition to a stabilizing function, the photographic reagent AH may be a development inhibitor, toning agent, antistatic agent, mordanting agent, metal complexing agent, or the like, A being the residue of that compound found by the removal of a hydrogen.

Michael donors AH useful in the invention are of various types, and include the sulfur and nitrogen nucleophiles described in U.S. Pat. Nos. 4,485,236 and 4,639,286, incorporated herein by reference, and those described in application File No. 45053USA1A. These Michael donors include carbon nucleophiles such as carbon acids with a pka of less than 15 and enamines.

A useful reference for obtaining information regarding the acidities, i.e., pKa's, of organic compounds is "Ionisation Constants of Organic Acids in Aqueous Solution" by E. P. Serjeant and B. Dempsey, IUPAC Chemical Data Series No. 23, Pergamon Press: Oxford, 1979. formulas of representative useful carbon acidic compounds which possess pKa's less than 15 and/or are suitably activated by having the carbon acidic function contained within a ring system of 6 atoms or less include the following, with estimated portions of the reactive hydrogen on the AH group being noted for informational, non-limiting purposes only:

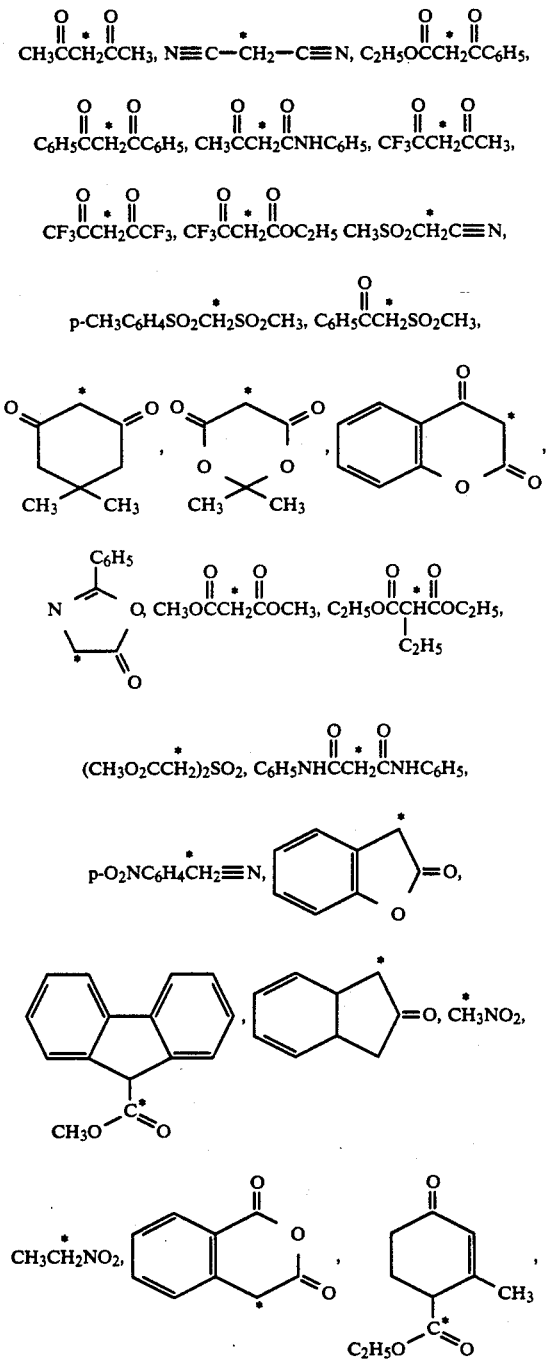

Another series of representative carbon acids useful in the invention include the reaction products of amines/alcohols/mercaptans and diketene. Amine reactants can be relatively simple such as mono-, di- and triamines or relatively complex polymeric amines. The preparation of these useful adducts is disclosed in South African patent 85 2506 and is incorporated herein by reference. Examples of carbon acids prepared in this fashion include the following:

$$CH_3CCH_2CNH-(CH_2)_6-NHCCH_2CCH_3,$$

$$n\text{-}C_{18}H_{37}NHCCH_2CCH_3, \text{ and}$$

$$CH_2O(CH_2CHO)_{17}CH_2CHNHCCH_2CCH_3$$
$$CHO(CH_2CHO)_{17}CH_2CHNHCCH_2CCH_3$$
$$CH_2O(CH_2CHO)_{17}CH_2CHNHCCH_2CCH_3.$$

Formulas of useful enamine compounds include:

Nitrogen nucleophiles useful as Michael donors in the instant invention include acylsulfonamides and the imidic, thio-imidic and selected nitrogen heterocycles including:

$$CH_3-\!\!\!\!\!\bigcirc\!\!\!\!\!-SO_2NHCO_2C_2H_5,$$

-continued
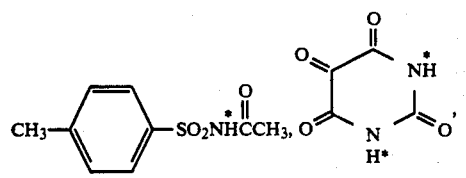
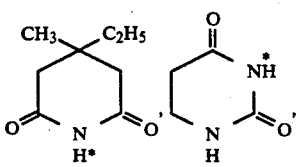
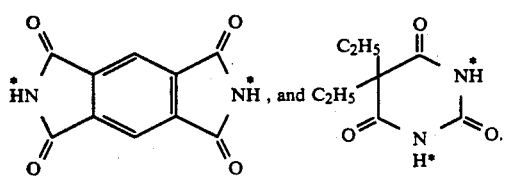
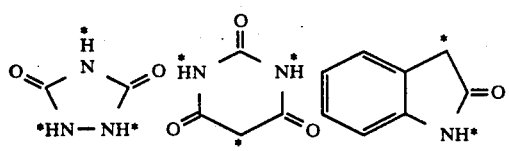
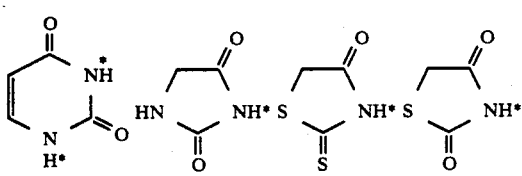
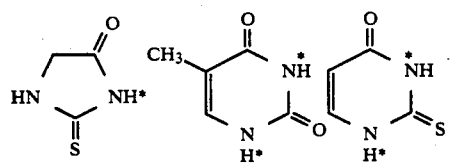
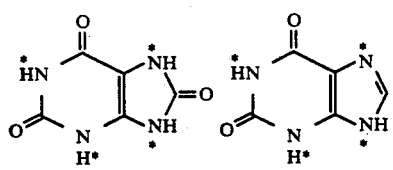
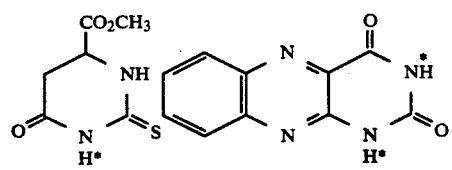
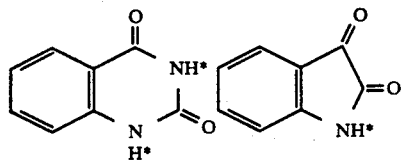
-continued
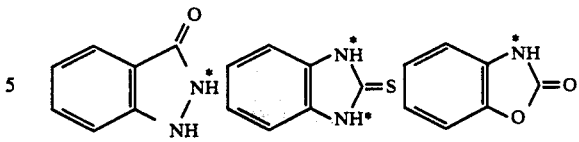
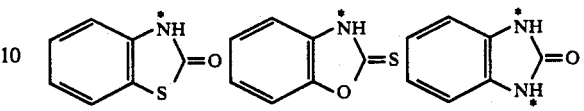
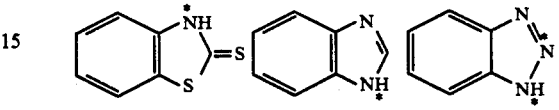
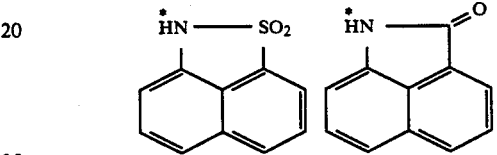
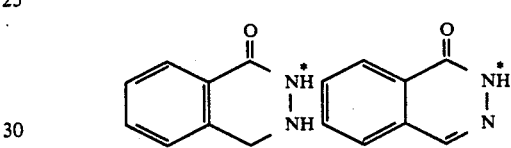
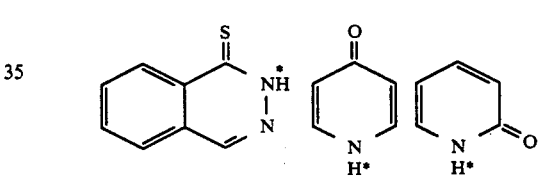
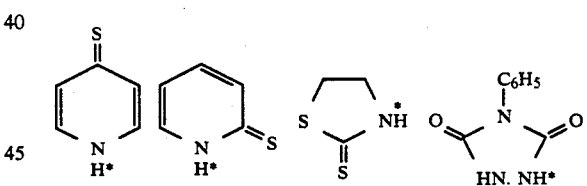
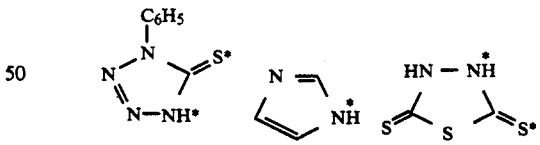
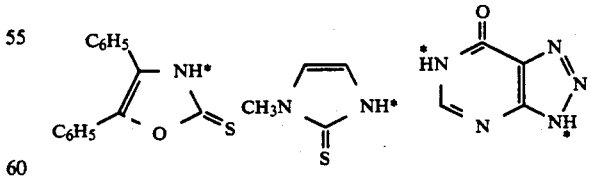
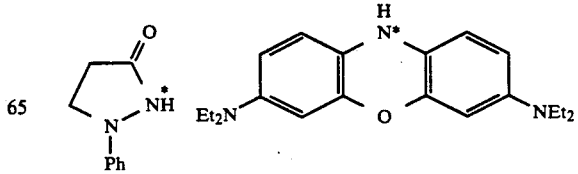

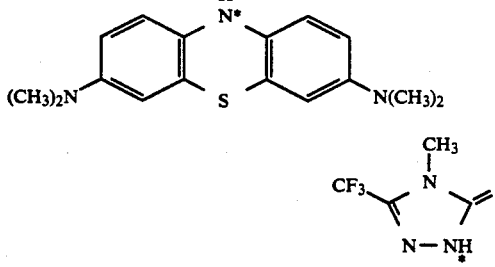

In those compounds containing both sulfur and nitrogen Michael donor groups such as 1-phenyl-1H-tetrazole-5-thiol, 2-mercaptobenzimidazole, or 2-mercaptobenzothiazole, reaction conditions can influence the site of reaction as exemplified in the Examples below.

Especially useful Michael acceptors of the invention are 2-alkenyl azlactone compounds represented by Formula V. Examples of suitable 2-alkenyl azlactones include 2-vinyl-4,4-dimethyl-2-oxazolin-5-one [or 2-vinyl-4,4-dimethylazlactone (VDM)], 2-isopropenyl-4,4-dimethyl-2-oxazolin-5-one, 2-vinyl-4-ethyl-4-methyl-2-oxazolin-5-one, 2-vinyl-4,4-dimethyl-1,3-oxazin-6-one, and others disclosed in U.S. Pat. No. 4,304,705 which is incorporated herein by reference. A preferred 2-alkenyl azlactone is VDM (available from SNPE, Inc., Princeton, N.J.).

Other useful Michael acceptors of the invention are the acrylamide compounds that can result from the ring opening reaction of a 2-alkenyl azlactone of Formula V by a nucleophile HXG as represented below.

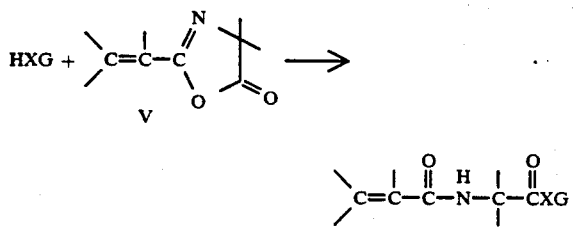

Representative HXG compounds of the invention include any soluble or insoluble, low or high molecular weight compound that contains at least one nucleophilic group, such as those described in application File No. 44848USA6A, incorporated herein by reference including also:

1) Alcohols.

Useful soluble, low molecular weight alcohols include methanol, ethanol, n-propanol, isopropanol, n-butanol, cyclohexanol, benzyl alcohol, dodecanol, hexadecanol, ethylene glycol, 1,3-propanediol, pentaerythritol, and trimethylolpropane.

Useful high molecular weight oligomeric and polymeric alcohols are disclosed in U.S. Pat. No. 4,874,822, incorporated herein by reference and include:

(a) Polyether polyols such as polyethylene oxide and polypropyleneoxide based polyols (including the polyethoxylates of aliphatic alcohols and amines, alkyl phenols, and fatty acids and amides), Polyethyleneoxide/propyleneoxide copolymer polyols, and polytetramethyleneoxide based polyols;

(b) Polyester polyols, such as polycaprolactone polyols, polyneopentyladipate polyols, or other hydroxy functional polycarboxylic ester oligomers and polymers;

(c) Polysiloxane polyols such as those described in U.S. Pat. Nos. 4,098,742; 3,886,865; 3,577,264; and 4,013,698;

(d) Polycarbonate polyols such as the Duracarb TM series of polyols from PPG Industries Inc., Chicago, Ill.;

(e) Hydroxy functional polyacrylic and methacrylic ester polymers, such as those prepared according to U.S. Pat. Nos. 4,414,372; 4,417,034; 4,508,880; and 4,524,196;

(f) Phenolic resins, particularly the phenol/formaldehyde condensates referred to collectively as "resols", which contain —CH$_2$OH functionality;

(g) Polymers and copolymers of hydroxy functional vinyl monomers such as 2-hydroxyethyl acrylate, 2-hydroxyethyl methacrylate, hydroxypropyl acrylate, 2-hydroxyethyl acrylamide, 2-hydroxyethyl maleimide, 4-hydroxybutyl vinyl ether, glycerol monoacrylate or methacrylate, pentaerythritol monoacrylate, and diethyleneglycol monomethacrylate; these polymers include homopolymers of the hydroxy functional vinyl monomers as well as copolymers derived from copolymerization of the hydroxy functional vinyl monomers with one or more of a variety of comonomers. Suitable comonomers include essentially any free radically polymerizable ethylenically unsaturated monomers, examples of which include: the vinyl aromatic monomers such as styrene, α-methylstyrene, 2- and 4-vinyl pyridine, and the like; α-β-unsaturated carboxylic acids and their derivatives such as acrylic acid, methacrylic acid, itaconic acid, maleic acid, fumaric acid, crotonic acid, methyl methacrylate, butyl methacrylate, 2-ethylhexyl methacrylate, ethyl acrylate, butyl acrylate, iso-octyl acrylate, octadecyl acrylate, cyclohexyl acrylate, tetrahydrofurfuryl methacrylate, phenyl acrylate, phenethyl acrylate, benzyl methacrylate, β-cyanoethyl acrylate, maleic anhydride, diethyl itaconate, acrylamide, methacrylonitrile, N-butylacrylamide, and the like; vinyl esters of carboxylic acids such as vinyl acetate, vinyl 2-ethylhexanoate, and the like; vinyl halides such as vinyl chloride, vinylidene chloride, and the like; vinyl ethers such as ethyl vinyl ether, butyl vinyl ether, 2-ethylhexyl vinyl ether, and the like; olefins such as ethylene, N-vinyl compounds such as N-vinylpyrrolidone, N-vinylcarbazole, and the like; vinyl ketones such as methyl vinyl ketone and the like; and vinyl aldehydes such as acrolein, methacrolein, and the like;

(h) Polymers and copolymers derived form vinyl acetate, vinyl trifluoroacetate, or other vinyl esters, such as vinyl acetate/vinyl alcohol copolymers, polyvinyl alcohol, polyvinyl acetal, polyvinyl butyral, and other hydrolyzed or partially hydrolyzed vinyl ester copolymers;

(i) Cellulose and modified cellulose polymers such as cellulose acetate, cellulose nitrate, cellulose acetate propionate, cellulose acetate butyrate, cellulose acetate phthalate, hydroxypropyl cellulose, hydroxyethyl cellulose, benzyl cellulose, methyl cellulose, and ethyl cellulose; and (j) Phenoxy polymers, such as those prepared by step-growth polymerization of bisphenol A diglyoidyl ether or other diepoxides with bisphenols.

2) Substantially perfluorinated alcohols.

Useful 1,1-dihydroperfluorinated alcohols include those disclosed in U.S. Pat. No. 4,906,792, incorporated herein by reference.

3) Water.
4) Thiols.

Useful soluble, low molecular weight thiols include dodecyl mercaptan, thiophenol, 2-mercaptoethyl ether, and pentaerythritol tetrathioglycolate. Useful soluble, high molecular weight thiols include polyethylene glycol di(2-mercaptoacetate), LP ™-3 resins supplied by Morton Thiokol Inc. (Trenton, N.J.), and Permapol ™ P3 resins supplied by Products Research & Chemical Corp. (Glendale, Calif.). Useful insoluble thiol compounds include the soluble, high molecular weight thiols previously mentioned that have been crosslinked by a variety of techniques which retain thiol functional groups such as ionizing radiation. Another useful insoluble thiol compound is the reaction product of chloromethylated copoly(styrene-devinylbenzene) and thiourea disclosed by Frechet, et al., *Polymer*, 20, 675 (1979), incorporated herein by reference.

5) Phenols.

Useful soluble low molecular weight phenols include phenol, p-methoxyphenol, p-phenylazophenol, cresol, p-dodecylphenol, p-fluorophenol, p-trifluoromethylphenol, p-nitrophenol, and 8-hydroxyquinoline. Useful soluble, high molecular weight phenols include poly(p-hydroxystyrene) and resole and novalac resins, prior to final cure. After cure these latter crosslinked phenol-formaldehyde polymers are useful insoluble phenol compounds. Another useful insoluble phenol compound is the reaction product of lithiated copoly(styrene-divinylbenzene) and oxygen also disclosed by Frechet, et al., ibid.

6) Primary and secondary amines.

Useful primary amines include methylamine, ethylamine, propylamine, butylamine, cyclohexylamine, benzylamine, dodecylamine, and aniline. Useful secondary amines include diethylamine, piperidine, morpholine, and N-methylaniline. Useful oligomeric and polymeric amines include those disclosed in U.S. Pat. No 4,837,290, incorporated herein by reference. Also useful amines are amidine compounds such as benzamidine and 2-methylimidazoline and guanidine compounds such as tetramethylguanidine.

The omega-substituted-2-propioamidoacetyl and omega-substituted-3-propioamidopropionyl compositions of the instant invention are most easily prepared by in a two step process. The first step of this process (Process 1) involves the reaction of a Michael donor, AH, with a 2-alkenyl azlactone Michael acceptor (VIII) to provide an azlactone Michael adduct of Formula IX. In a second step, a nucleophile HXG is reacted with the azlactone Michael adduct of Formula IX to provide the compositions of the invention:

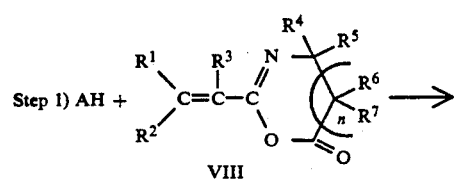

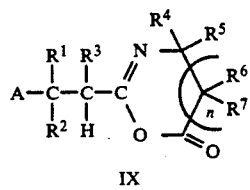

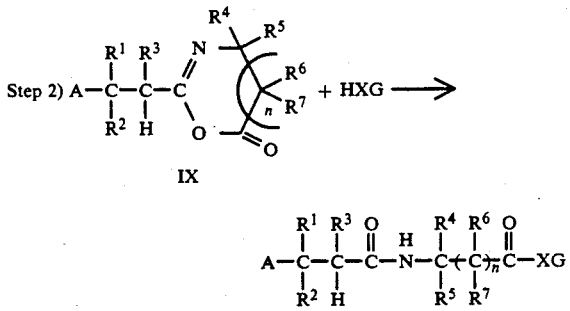

(wherein A, $R^1$, $R^2$, $R^3$, $R^4$, $R^5$, $R^6$, $R^7$, X, G, and n are as described above).

Conditions for effecting the Michael reaction of 2-alkenyl azlactones with Michael donors, AH, can vary considerably depending on the nature of AH.

Reactions are preferably conducted in the absence of solvent, but if a solvent is required to form a homogeneous reaction solution, the solvent should not react with the reactants or products. Suitable solvents include ethyl acetate, methyl ethyl ketone, toluene, chloroform, tetrahydrofuran, N,N-dimethylformamide, N,N-dimethylacetamide, N-methylpyrrolidinone, xylene, decalin, chlorobenzene, and glymes. The amount of solvent employed should be as small as possible because dilution of reactants slows reaction rate. Useful amounts of solvent employed are from 0.9 to 0.1, preferably 0.7 to 0.1, and more preferably 0.5 to 0.1 weight fraction of the reaction solution.

Progress of the Michael reaction can be monitored by observing the disappearance of the absorbance of the carbon-carbon double bond of the 2-alkenyl azlactone Michael acceptor at about 1600 cm$^{-1}$ in the infrared spectrum.

It is sometimes advantageous to employ a catalyst in these reactions, and the most efficient catalysts are bicyclic amidines and trivalent phosphorus compounds described in U.S. Pat. No. 4,874,822 which is incorporated herein by reference.

Useful bicyclic amidine catalysts include 1,5-diazabicyclo[4.3.0]non-5-ene (DBN), 1,8-diazabicyclo[5.4.0]undec-7-ene (DBU), and 1,5,7-triazabicyclo[4.4.0]dec-5-ene (TBD), and useful trivalent phosphorous compounds include tributylphosphine and trioctylphosphine. DBN, DBU, and tributylphosphine are available from Aldrich Chemical Co. (Milwaukee, Wis.), and TBD and trioctylphosphine are available from Fluka Chemical Corp. (Ronkonkoma, N.Y.). Effective amounts of the catalyst are from 0.1 to 10.0 mole percent (based on 2-alkenyl azlactone), preferably 1.0 to 7.0 mole percent, and more preferably 2.0 to 5.0 mole percent. While with some of the more acidic and reactive carbon acids Michael reaction proceeds exothermically at room temperature, it is often useful to warm the reaction mixture from 50° C. to 150° C. for periods of up to 72 hours.

Step 2 of this process for making the compositions of the invention involves addition of a nucleophile, HXG, to the azlactone Michael adduct of Formula IX to cause a ring opening reaction. This is most easily effected by mixing the nucleophile, HXG, with the azlactone Michael adduct of Formula IX. Although the azlactone Michael adduct of Formula IX may be isolated and purified prior to this step, this is optional and not usually necessary. Reaction of HXG with the azlactone Michael adduct of Formula IX is carried out either in the presence of absence of a solvent and optionally in the presence of a catalyst. Whether this reaction occurs in a reasonable amount of time, e.g., <24 hours, is largely determined by the nucleophile (HXG), the presence of a catalyst, the reaction temperature, and the concentration of the reactants. The most reactive HXG nucleophiles of the invention are the guanidines and amidines, and they generally require no catalyst for efficient addition to azlactone compounds at room temperature. Reactions of amines and water generally proceed at reasonable rates in the presence of Bronsted acidic catalysts such as trifluoroacetic acid, p-toluenesulfonic acid, and ethanesulfonic acid, employed in concentrations of from 0.1 to 10 mole percent (based on reactant). Alcohols, thiols, phenols, and 1,1-dihydroperfluorinated alcohols generally add efficiently in the presence of cyclic amidine bases such as 1,8-diazabicyclo[5.4.0]undec-7-ene (DBU) and 1,5-diazabicyclo[4.3.0]non-5-ene (DBN), employed in the same concentrations as the acidic catalysts. When the addition reaction is slow at room temperature, elevating the temperature increases reaction rate; useful temperatures are from 22°–80° C. If solvents are employed, they should not react with either the nucleophile or the azlactone, and suitable organic solvents include ethyl acetate, methyl ethyl ketone, toluene, chloroform, dichloromethane, and tetrahydrofuran. Furthermore, the amount of solvent employed should be as small as possible because dilution of reactants slows reaction rate. Useful amounts of solvent employed are from 0.9 to 0.1, preferably 0.7 to 0.1, and most preferably 0.5 to 0.1 weight fraction of the reaction solution. Progress of the reaction is conveniently monitored by observing the disappearance of the strong and characteristic azlactone carbonyl absorption band in the infrared at about 1800 cm$^{-1}$.

As an alternative to the Process I outlined above, the compositions of the invention may be prepared by an alternative two step process (Process II). In Process II, Step 1 involves the addition of a nucleophile, HXG, to a 2-alkenyl azlactone (VIII) to cause a ring opening reaction and produce an acrylamide of Formula X. Step 2 of this process involves Michael-addition of a Michael donor, AH, to the carbon-carbon double bond of the acrylamide of Formula X.

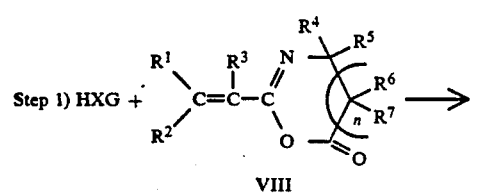

VIII

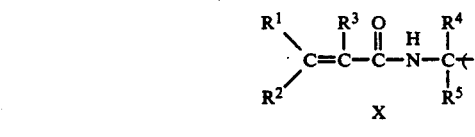

X

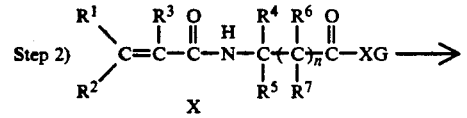

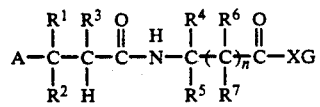

(wherein A, $R^1$, $R^2$, $R^3$, $R^4$, $R^5$, $R^6$, $R^7$, X, G, and n are as described above).

Conditions for effecting the ring-opening reaction and Michael-addition reaction of Process II are the same as those described for the respective reactions in Process I. In general, Process I is simpler and more general than Process II because the 2-alkenyl azlactones of Formula VIII are more reactive Michael acceptors than are the acrylamides of Formula X.

Finally, in a third process (Process III) it is sometimes possible to prepare the compositions of the invention by a one-step process that involves mixing of a 2-alkenyl azlactone of Formula VIII with a Michael donor, AH, and a nucleophile, HXG, optionally in the presence of catalysts and solvents described above and optionally with heating. This third process is feasible only in those instances when AH and HXG are not of comparable reactivity; that is, when AH does not lead to ring opening and HXG does not function as a Michael donor.

Although the compositions of the invention are most easily prepared by the methods described above, it is also contemplated as within the scope of the invention to provide these compositions by condensations of HXG nucleophiles with the acids of Formula XI:

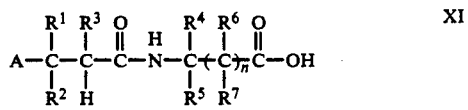

(wherein A, $R^1$, $R^2$, $R^3$, $R^4$, $R^5$, $R^6$, $R^7$, and n are as described above).

In these reactions standard condensation reagents such as dicyclohexylcarbodiimide or ethyl chloroformate may be employed.

Utility of the omega-substituted-2-propioamidoacetyl and omega-substituted-3-propioamidopropionyl compositions of the instant invention derives from their ability to function as blocked, protected, or ballasted photographic reagents which appear to be unblocked by the application of heat during processing. In another sense, the 2-propioamidoacetyl and 3-propioamidopropionyl portions of the compositions of the instant invention function as secondary stabilizers and contribute to post processing stability.

Objects and advantages of this invention are further illustrated by the following examples, but the particular materials and amounts thereof recited in these examples, as well as other conditions and details, should not be construed to unduly limit the invention.

Preparation of the compounds of Formula I is described in Examples 1 through 62, below. In all cases, structures of the compounds were confirmed by spectral analysis, including IR, proton, and carbon NMR spectroscopy. Application of the novel compounds to improve the quality of imaging constructions are detailed in Examples 63 through 67, below. In Examples 63 through 67, the relevant compound is referred to by that compound's number in the preparative examples.

EXAMPLE 1

This example teaches the preparation of a blocked benzotriazole by Process I.

A mixture of VDM (2-vinyl-4,4-dimethylazlactone) (13.9 g, 0.10 mole) and benzotriazole (11.9 g, 0.10 mole) was heated at 100° C. overnight, then phenol (9.4 g, 0.10 mole) and DBU (0.2 g) were added and heating continued for 24 hours at 100° C. Recrystallization from aqueous ethanol gave the product as a mixture of 1-N-alkylated and 2-N-alkylated isomers as shown below in about a 4 to 1 ratio.

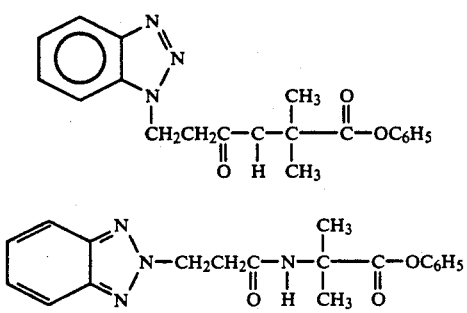

EXAMPLE 2

This example teaches the preparation of the blocked benzotriazole of Example 1 by Process II.

To a mixture of VDM (13.9 g, 0.10 mole) and phenol (9.4 g, 0.10 mole) was added 0.3 g of DBU. After 1 hour, benzotriazole (11.9 g, 0.10 mole) was added and the mixture heated at 125° C. for 48 hours to provide the desired product as a mixture of 1-N-alkylated and 2-N-alkylated products as a mixture of isomers.

EXAMPLE 3

This example teaches the preparation of the blocked benzotriazole of Example 1 by Process III.

A reaction vessel was charged with benzotriazole (11.9 g, 0.10 mole), phenol (9.4 g, 0.10 mole), VDM (13.9 g, 0.10 mole), and DBU (0.3 g). After 1 hour at room temperature, the mixture was heated at 100° C. for 48 hours to provide the desired product as a mixture of 1-N-alkylated and 2-N-alkylated products as a mixture of isomers.

Examples 4 and 5 teach that reaction conditions may be controlled to achieve blocking on either sulfur or nitrogen of a mercaptotetrazole.

EXAMPLE 4

This example teaches preparation of a sulfur blocked mercaptotetrazole.

VDM (13.9 g, 0.10 mole) was cooled to 0° C. and mixed with 1-phenyl-1H-tetrazole-5-thiol (17.8 g, 0.10 mole). The mixture was allowed to warm to room temperature and kept at this temperature overnight. The white solid was dissolved in acetone (100 ml), water (10 ml) was added, and the mixture allowed to stand at room temperature overnight. After evaporation of solvent, the product was recrystallized from ethanol-water. Spectral analyses confirmed the structure as that shown below:

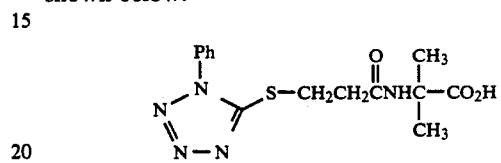

EXAMPLE 5

This example teaches preparation of a nitrogen blocked mercaptotetrazole.

VDM (13.9 g, 0.10 mole) and 1-phenyl-1H-tetrazole-5-thiol (17.8 g, 0.10 mole) were heated at 100° C. for 24 hours. The product was dissolved in acetone (100 ml), water (10 ml) was added, and the mixture allowed to stand at room temperature overnight. After evaporation of solvent, the product was recrystallized from ethanol-water. Spectral analyses confirmed the identity of the product as the nitrogen-alkylated compound shown below.

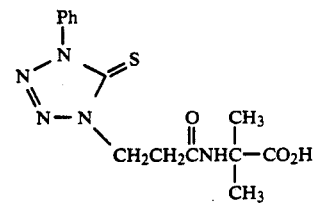

EXAMPLES 6–62

The following examples were prepared by Process 1 with reaction conditions analogous to those described in Example 1.

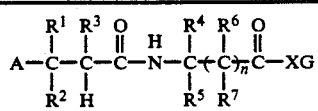

| Ex. | A | R¹ | R² | R³ | R⁴ | R⁵ | R⁶ | R⁷ | n | XG |
|---|---|---|---|---|---|---|---|---|---|---|
| 6 |  | H | H | H | CH₃ | CH₃ | — | — | 0 | —OH |
| 7 | " | " | " | " | " | " | " | " | " | —O—⟨C₆H₄⟩—CH₃ |

-continued $$A-\underset{\underset{H}{R^2}}{\overset{R^1}{C}}-\underset{\underset{H}{|}}{\overset{R^3}{C}}-\overset{O}{\overset{\|}{C}}-\underset{}{\overset{H}{N}}-\underset{\underset{R^5}{|}}{\overset{R^4}{C}}-(\underset{\underset{R^7}{|}}{\overset{R^6}{C}})_{\overline{n}}-\overset{O}{\overset{\|}{C}}-XG$$

| Ex. | A | R¹ | R² | R³ | R⁴ | R⁵ | R⁶ | R⁷ | n | XG |
|---|---|---|---|---|---|---|---|---|---|---|
| 8 | " | " | " | " | " | " | " | " | " |  |
| 9 | " | " | " | " | " | " | " | " | " |  |
| 10 | " | " | " | " | " | " | " | " | " | —OC₄H₉ |
| 11 | " | " | " | " | " | " | " | " | " | —OCH₂Ph |
| 12 | " | " | " | " | " | " | " | " | " | —OC₁₆H₃₃ |
| 13 | " | " | " | " | " | " | " | " | " |  |
| 14 | " | " | " | " | " | " | " | " | " | —N(H)—Ph |
| 15 | " | " | " | " | " | " | " | " | " | —N(CH₃)—Ph |
| 16 | " | " | " | " | " | " | " | " | " | —N(H)C₄H₉ |
| 17 | " | " | " | " | " | " | " | " | " | —N=C(N(CH₃)₂)(N(CH₃)₂) |
| 18 | 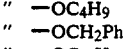 | " | " | " | " | " | " | " | " | —OH |
| 19 | " | " | " | " | " | " | " | " | " | —OPh |
| 20 | " | " | " | " | " | " | " | " | " |  |
| 21 | " | " | " | " | " | " | " | " | " | 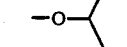 |
| 22 | " | " | " | " | " | " | " | " | " | 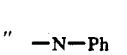 |

-continued $$A-\underset{\underset{R^2}{|}}{\overset{\overset{R^1}{|}}{C}}-\underset{\underset{H}{|}}{\overset{\overset{R^3}{|}}{C}}-\overset{\overset{O}{\|}}{C}-N-\underset{\underset{R^5}{|}}{\overset{\overset{R^4}{|}}{C}}-(\underset{\underset{R^7}{|}}{\overset{\overset{R^6}{|}}{C}})_n\overset{\overset{O}{\|}}{C}-XG$$

| Ex. | A | R¹ | R² | R³ | R⁴ | R⁵ | R⁶ | R⁷ | n | XG |
|---|---|---|---|---|---|---|---|---|---|---|
| 23 | " | " | " | " | " | " | " | " | " | 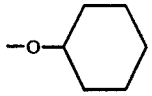 |
| 24 | " | " | " | " | " | " | " | " | " | —OC₄H₉ |
| 25 | " | " | " | " | " | " | " | " | " | —OCH₂CH₃ |
| 26 | " | " | " | " | " | " | " | " | " | —OC₁₆H₁₃ |
| 27 | " | " | " | " | " | " | " | " | " | —N(H)—Ph |
| 28 | " | " | " | " | " | " | " | " | " | —N(CH₃)—Ph |
| 29 | " | " | " | " | " | " | " | " | " | —N(H)C₄H₉ |
| 30 | " | " | " | " | " | " | " | " | " | —N=C(N(CH₃)₂)(N(CH₃)₂) |
| 31 |  | " | " | " | " | " | " | " | " | —OC₄H₉ |
| 32 | " | " | " | " | " | " | " | " | " | —OCH₂CF₃ |
| 33 | " | " | " | " | " | " | " | " | " |  |
| 34 |  | " | " | " | " | " | " | " | " | —OCH₂CF₃ |
| 35 | " | " | " | " | " | " | " | " | " | —OC₄H₉ |
| 36 | " | " | " | " | " | " | " | " | " | 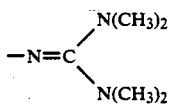 |
| 37 | 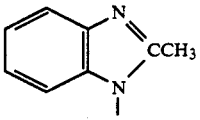 | " | " | H | " | " | " | " | " | —OH |
| 38 | " | " | " | " | " | " | " | " | " | 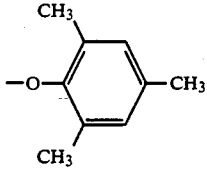 |

-continued $$A-\underset{R^2}{\underset{|}{\overset{R^1}{\underset{|}{C}}}}-\underset{H}{\overset{R^3}{\underset{|}{C}}}-\overset{O}{\overset{\|}{C}}-\underset{}{\overset{H}{\underset{|}{N}}}-\underset{R^5}{\underset{|}{\overset{R^4}{\underset{|}{C}}}}(\underset{R^7}{\underset{|}{\overset{R^6}{\underset{|}{C}}}})_n\overset{O}{\overset{\|}{C}}-XG$$

| Ex. | A | R¹ | R² | R³ | R⁴ | R⁵ | R⁶ | R⁷ | n | XG |
|---|---|---|---|---|---|---|---|---|---|---|
| 39 | " | " | " | " | " | " | " | " | " | —OCH₂Ph |
| 40 | (2-methyl-1-oxo-phthalazine) | " | " | " | " | " | " | " | " | —OCH₂CF₃ |
| 41 | " | " | " | " | " | " | " | " | " | —OC₄H₉ |
| 42 | " | " | " | " | " | " | " | " | " | —OC₁₆H₃₃ |
| 43 | " | " | " | " | " | " | " | " | " | —OPh |
| 44 | " | " | " | " | " | " | " | " | " | —OCH(CF₃)₂ |
| 45 | " | " | " | " | " | " | " | " | " | —CH₂-(1,4-difluoro-perfluorocyclohexyl)F₁₀ |
| 46 | " | " | " | " | " | " | " | " | " | —OCH₂C₇F₁₅ |
| 47 | (2-methyl-1-oxo-phthalazine) | " | " | " | " | " | " | " | " | —N(H)C₄H₉ |
| 48 | " | " | " | " | " | " | " | " | " | —N(H)Ph |
| 49 | " | " | " | " | " | " | " | " | " | —N(CH₃)Ph |
| 50 | " | " | " | " | " | " | " | " | " | —N=C(N(CH₃)₂)₂ |
| 51 | (1-phenyl-4-methyl-5-thio-tetrazole) | " | " | " | " | " | H | H | 1 | —OH |
| 52 | " | " | " | " | " | " | — | — | 0 | —OPh |
| 53 | " | " | " | " | " | " | " | " | " | —OH |
| 54 | (1-phenyl-4-methyl-5-thio-triazole) | " | " | " | " | " | " | " | " | —N=C(N(CH₃)₂)₂ |
| 55 | (4-methyl-5-trifluoromethyl-3-thio-triazole) | " | " | " | " | " | " | " | " | —OH |
| 56 | " | " | " | " | " | " | " | " | " | —OCH₂CF₃ |

-continued

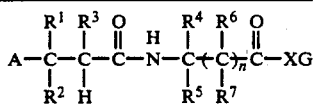

| Ex. | A | R¹ | R² | R³ | R⁴ | R⁵ | R⁶ | R⁷ | n | XG |
|---|---|---|---|---|---|---|---|---|---|---|
| 57 | " | " | " | " | " | " | " | " | " | —$OC_4H_9$ |
| 58 | " | " | " | " | " | " | " | " | " | —OPh |
| 59 | " | " | " | " | " | " | " | " | " | —O—C₆H₄—$OCH_3$ |
| 60 | (triazoline-thione structure) | " | " | " | " | " | " | " | " | —O—(2,4,6-trimethylphenyl) |
| 62 | (phthalazinone structure) | " | " | " | " | " | " | " | " | —$OCH_2CF_3$ |
| 62 | (1-phenyl-3-pyrazolidinone structure) | " | " | " | " | " | " | " | " | —OH |

Advantages of the compositions of the present invention will be illustrated in detail by the following non-limiting examples. Description of specific imaging protocols may be found in Application File No. 45444USA1A.

EXAMPLE 63

A dispersion of silver behenate half soap was made at 10% solids in toluene and acetone by homogenization. To 127 g of this silver half soap dispersion was added 252 g methyl ethyl ketone, 104 g isopropyl alcohol and 0.5 g of polyvinylbutyral. After 15 minutes of mixing 4 ml of mercuric bromide (0.36/10 ml methanol) were added. Then 8.0 ml of calcium bromide (0.236 g) 10 ml methanol was added 30 minutes later. After two hours of mixing, 27.0 g of polyvinylpyrolidone was added, and 27.0 g of polyvinylbutyral was added one hour later.

To 32.1 g of the prepared silver premix described above was added 2.0 ml of the sensitizing dye A (0.045 g/50 ml of methanol) shown below.

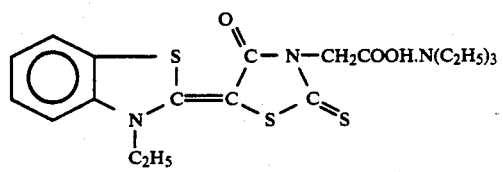

A

After 20 minutes a yellow color forming leuco dye solution was added as shown below.

| Component | Amount |
|---|---|
| Leuco Dye B | 0.275 g |
| Tribenzylamine | 0.24 g |
| Phthalazinone | 0.14 g |
| Tetrahydrofuran | 6.0 ml |

The leuco dye is disclosed in U.S. Pat. No. 4,883,747 and has the following formula:

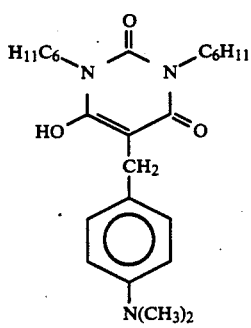

B

After sensitization with the dye and the addition of the leuco base dye solution compound 52 was added in the amounts of 0.2 ml or 0.5 ml at a concentration of 0.2 g/5 ml of methanol to 9.9 g aliquot of the yellow coating solution. The resulting solutions were coated along with a solution not containing any stabilizer precursor at a wet thickness of 3 mils and dried at 82° C. in an oven for 5 minutes onto a vesicular polyester base. A topcoat solution was coated at a wet thickness of 3 mils over the silver halide layer and dried at 82° C. in an oven for 5 minutes. The topcoat solution consisted of 7% polyvinyl alcohol in an approximate 50:50 mixture of water and methanol and 0.06% phthalazine.

The samples were exposed for $10^{-3}$ seconds through a 47B Wratten filter and a 0 to 3 continuous wedge and developed by heating to approximately 138° C. for 6 seconds. The density of the dye was measured using a blue filter of a computer densitometer. Post processing stability was measured by exposing imaged samples to 1200 ft. candles of illumination for 6 hours at 65% relative humidity and 26.7° C. The initial sensitometric data are shown below:

|  | Dmin | Dmax | Speed[1] | Contrast[2] |
|---|---|---|---|---|
| Control (0.0 ml) | 0.11 | 2.46 | 1.77 | 5.09 |
| 0.2 ml 52 | 0.12 | 2.55 | 1.70 | 5.90 |
| 0.5 ml 52 | 0.13 | 2.54 | 1.72 | 5.78 |

[1]Log exposure corresponding to density of 0.6 above Dmin.
[2]Average contrast measured by the slope of the line joining density points 0.3 and 0.9 above Dmin.

The post-processing print stability results are shown below.

|  | ΔDmin | ΔDmax |
|---|---|---|
| Control (0.0 ml) | +0.48 | −0.02 |
| 0.2 ml 52 | +0.46 | −0.03 |
| 0.5 ml 52 | +0.38 | −0.02 |

A 20% improvement in the post processing Dmin was observed vs. the unstabilized control with little effect on the initial sensitometric response.

EXAMPLE 63A (comparison)

To 9.9 g of the yellow silver halide coating solution as described in Example 63, was added 1.0 ml of 1-phenyl-5-mercapto-tetrazole (PMT) at a concentration of 0.1 g/5 ml of methanol. The silver solutions and topcoats were coated, exposed, and processed as described in Example 63. The initial sensitometric data are shown below.

|  | Dmin | Dmax | Speed[1] | Contrast[2] |
|---|---|---|---|---|
| Control (0.0 ml) | 0.14 | 2.52 | 1.73 | 5.01 |
| 0.1 ml PMT | 0.12 | 1.02 | 2.36 | 0.36 |

[1]Log exposure corresponding to density of 0.6 above Dmin.
[2]Average contrast measured by the slope of the line joining density points 0.3 and 0.9 above Dmin.

The post-processing print stability results are shown below.

|  | ΔDmin | ΔDmax |
|---|---|---|
| Control (0.0 ml) | +0.50 | −0.06 |
| 0.1 ml PMT | +0.18 | −0.11 |

At this concentration of PMT, significant desensitization of the silver halide emulsion as occurred for post-processing Dmin improvements. In Example 63, PMT was blocked by the ring opened azlactone group to minimize any desensitization effects but still allowed release of some PMT for Dmin post-processing improvements.

EXAMPLE 64

A magenta color-forming silver halide dispersion was prepared by using 502 g of the silver half soap dispersion of Example 63 and adding 0.4 g of polyvinylbutyral. After 15 minutes of mixing, a 0.5 g/9.75 g mercuric acetate in methanol solution and a 0.55 g/18.4 g calcium bromide in methanol solution were added. Then an additional 0.55 g/18.4 g calcium bromide in methanol solution was added 30 minutes later. After 45 minutes of mixing, 49.8 g of polyvinylbutyral was added to provide a silver premix.

To 35.8 g of the prepared silver premix described above was added 1.4 ml of the sensitizing dye C (0.02 g/100 ml of methanol) shown below.

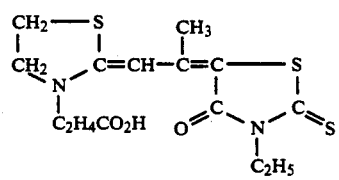

C

After 30 minutes, a magenta color-forming leuco dye solution was added as shown below.

| Component | Amount |
|---|---|
| Leuco D | 0.593 g |
| Phthalazinone | 0.901 g |
| Tetrahydrofuran | 47.6 g |
| VAGH (Union Carbide) | 2.2 g |
| Polyvinylbutyral | 10.2 g |

The leuco dye D is disclosed in U.S. Pat. No. 4,795,697 and has the following formula

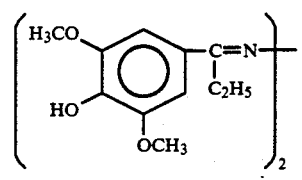

D

A topcoat solution was prepared consisting of 24.0% polystyrene resin in approximately 50% tetrahydrofuran, 7% toluene, 2% acetone and 5% methanol.

To 10.0 g of the magenta silver coating solution was added 0.67 ml or 1.0 ml of the isomer mixture, compounds 1, at a concentration of 0.3 g/3 ml of methanol and 2 ml of tetrahydrofuran, or 0.65 ml of benzotriazole (BZT) at a concentration of 0.1 g/5 ml of methanol. The magenta silver layer and topcoat are coated simultaneously at a wet thickness of 2 mils, respectively and dried for 5 minutes 82° C.

The samples were exposed for $10^{-3}$ seconds through a 58 Wratten filter and a 0 to 3 continuous wedge and developed by heating to approximately 138° C. for 6 seconds.

The density of the dye for each sample was measured using a green filter of a computer densitometer. Post-processing stability was measured by exposing imaged samples to 1200 ft.-candles of illumination for 7 hours at 65% relative humidity and 26.7° C. The initial sensitometric data are shown below.

|  | Dmin | Dmax | Speed[1] | Contrast[2] |
|---|---|---|---|---|
| Control (0.0 ml) | 0.08 | 1.92 | 1.93 | 2.03 |
| 0.65 ml BZT | 0.08 | 0.20 | — | — |
| 0.67 ml 1 | 0.08 | 1.98 | 1.98 | 2.03 |
| 1.0 ml 1 | 0.08 | 1.89 | 2.02 | 2.01 |

[1] Log exposure corresponding to density of 0.6 above Dmin.
[2] Average contrast measured by the slope of the line joining density points 0.3 and 0.9 above Dmin.

The post-processing print stability results are shown below.

|  | ΔDmin | ΔDmax |
|---|---|---|
| Control (0.0 ml) | +0.18 | −0.16 |
| 0.65 ml BZT | +0.13 | — |
| 0.67 ml 1 | +0.16 | −0.14 |
| 1.0 ml 1 | +0.14 | −0.21 |

At this concentration of benzotriazole, Dmin post-processing improvements are observed, but significant densitization of the silver halide emulsion has occurred. With the addition of 1, BZT has been adequately blocked to minimize any desensitization and yet release of BZT occurred at the appropriate time for Dmin post-processing improvements similar to the unblocked BZT stabilizer.

EXAMPLE 65

To 10.0 g of the magenta silver halide coating solution, as described in Example 64, was added 0.95 ml of compound 18 at a concentration of 0.1 g/2.5 ml methanol and 2.5 ml tetrahydrofuran or 0.65 ml of benzimidazole (BI) at a concentration of 0.1 g/5 ml of methanol. The silver solutions and topcoats were coated, exposed, and processed as described in Example 64. The initial sensitometric data are shown below.

|  | Dmin | Dmax | Speed[1] | Contrast[2] |
|---|---|---|---|---|
| Control (0.0 ml) | 0.08 | 1.92 | 1.93 | 2.03 |
| 0.65 ml BI | 0.08 | 1.59 | 2.64 | 1.94 |
| 0.95 ml 18 | 0.08 | 1.88 | 2.01 | 1.94 |

[1] Log exposure corresponding to density of 0.6 above Dmin.
[2] Average contrast measured by the slope of the line joining density points 0.3 and 0.9 above Dmin.

The post-processing print stability was measured as described in Example 64, and the results are shown below.

|  | ΔDmin | ΔDmax |
|---|---|---|
| Control (0.0 ml) | +0.18 | −0.16 |
| 0.65 ml BI | +0.14 | −0.27 |
| 0.95 ml 18 | +0.15 | −0.24 |

At this concentration of benzimidazole, Dmin post-processing improvements are observed with significant desensitization of the silver halide emulsion. With the addition of 18, BI has been adequately blocked to minimize any desensitization and yet release of the BI occurred at the appropriate time during processing for Dmin post-processing improvements similar to the unblocked BI stabilizer.

EXAMPLE 66

To 9.9 g of the yellow silver halide coating solution as described in Example 63, was added 0.2 ml or 1.0 ml of the isomer mixtures, compounds 13, at a concentration of 0.2 g/5 ml of methanol. The topcoat was similar to that described in Example 63. The silver solution and topcoats were coated, exposed and processed as described in Example 63. The initial sensitometric data are shown below.

|  | Dmin | Dmax | Speed[1] | Contrast[2] |
|---|---|---|---|---|
| Control (0.0 ml) | 0.12 | 2.49 | 1.90 | 5.64 |
| 0.2 ml 13 | 0.12 | 2.45 | 1.91 | 5.40 |
| 1.0 ml 13 | 0.11 | 2.32 | 1.96 | 5.28 |

[1] Log exposure corresponding to density of 0.6 above Dmin.
[2] Average contrast measured by the slope of the line joining density points 0.3 and 0.9 above Dmin.

The post-processing print stability results are shown below.

|  | ΔDmin | ΔDmax |
|---|---|---|
| Control (0.0 ml) | +0.56 | −0.10 |
| 0.2 ml 13 | +0.50 | −0.13 |
| 1.0 ml 13 | +0.34 | −0.17 |

A 40% improvement in the post-processing Dmin was observed vs. the unstabilized control with little effect on the initial sensitometric response.

EXAMPLE 66A (comparison)

To 9.9 g of the yellow silver coating solution as described in Example 66, was added 1.0 ml of benzotriazole (BZT) at a concentration of 0.1 g/5 ml in methanol. The topcoat was the same as used in Example 66, and the silver solutions and topcoats were coated, exposed and processed as described in Example 66. The initial sensitometric data are shown below.

|  | Dmin | Dmax | Speed[1] | Contrast[2] |
|---|---|---|---|---|
| Control (0.0 ml) | 0.12 | 2.22 | 1.84 | 4.52 |
| 1.0 ml BZT | 0.11 | 0.30 | | |

[1] Log exposure corresponding to density of 0.6 above Dmin.
[2] Average contrast measured by the slope of the line joining density points 0.3 and 0.9 above Dmin.

The post-processing print stability results are shown below.

|  | ΔDmin | ΔDmax |
|---|---|---|
| Control (0.0 ml) | +0.47 | −0.20 |
| 1.0 ml BZT | +0.17 | — |

At this concentration of BZT, significant desensitization of the silver halide emulsion has occurred for post-processing Dmin improvements. In Example 66, BZT was blocked by the ring opened azlactone group to minimize any desensitization effects but still allowed release of BZT at the appropriate time during processing for similar post-processing Dmin stabilization at the equivalent molar concentration as the unblocked BZT stabilizer.

EXAMPLE 67

To 9.9 g of the yellow silver halide coating solution as described in Example 63, was added 0.5 ml or 1.0 ml of compound 57 at a concentration of 0.44 g/5 ml of methanol, or 0.5 ml or 1.0 ml of 4-methyl-5-trifluoromethyl-4H-1,2,4-triazoline-3(2H)-thione (MFT) at a concentration of 0.2 g/5 ml of methanol. The topcoat was similar to that described in Example 63. The silver solution and topcoats were coated, exposed, and processed as described in Example 63. The initial sensitometric responses are shown below.

|                | Dmin | Dmax | Speed[1] | Contrast[2] |
| --- | --- | --- | --- | --- |
| Control (0.0 ml) | 0.09 | 2.42 | 1.96 | 5.00 |
| 0.5 ml MFT     | 0.09 | 1.90 | 2.12 | 4.11 |
| 1.0 ml MFT     | 0.09 | 0.10 | —    | —    |
| 0.5 ml 57      | 0.11 | 2.44 | 1.78 | 5.33 |
| 1.0 ml 57      | 0.11 | 2.29 | 1.82 | 5.71 |

[1]Log exposure corresponding to density of 0.6 above Dmin.
[2]Average contrast measured by the slope of the line joining density points 0.3 and 0.9 above Dmin.

The post-processing print stability results are shown below.

|                | ΔDmin  | ΔDmax  |
| --- | --- | --- |
| Control (0.0 ml) | +0.64 | −0.06 |
| 0.5 ml MFT     | +0.36 | −0.13 |
| 1.0 ml MFT     | +0.16 |       |
| 0.5 ml 57      | +0.39 | −0.07 |
| 1.0 ml 57      | +0.23 | −0.12 |

At these concentration of MFT, significant desensitization of the silver halide occurs with the Dmin post-processing stabilization. The blocking of MFT, as shown in compound 57, allows significant Dmin post-processing improvements similar to the equivalent molar amounts of the unblocked MFT stabilizer without losses in sensitivity.

Example 68 teaches that a ring-opened azlactone itself, i.e., the formal retro-Michael product from a compound of Formula I by the loss of AH, can act as a secondary stabilizer. In the Example below, compound 69 is the ring-opened product of VDM with phenol and compound 70 isi the ring-opened product of VDM with 2,2,2-trifluoroethanol.

EXAMPLE 68

To 9.9 g of the yellow silver solution described in Example 67, was added 1.0 ml of compound 69 or 1.0 ml of compound 70 at a concentration of 0.255 g/3 ml of ethanol and 2 ml tetrahydrofuran and 0.26 g/3 ml of methanol and 2 ml tetrahydrofuran, respectively. The topcoat was the same as described in Example 67, and the silver solutions and topcoats were coated, exposed, and processed as described in Example 63. The initial sensitometric data are shown below.

|                | Dmin | Dmax | Speed[1] | Contrast[2] |
| --- | --- | --- | --- | --- |
| Control (0.0 ml) | 0.11 | 2.42 | 1.85 | 5.57 |
| 1.0 ml 69      | 0.11 | 2.32 | 1.74 | 5.35 |
| 1.0 ml 70      | 0.11 | 2.39 | 1.77 | 5.78 |

[1]Log exposure corresponding to density of 0.6 above Dmin.
[2]Average contrast measured by the slope of the line joining density points 0.3 and 0.9 above Dmin.

The post-processing print stability results are shown below.

|                | ΔDmin  | ΔDmax  |
| --- | --- | --- |
| Control (0.0 ml) | +0.51 | −0.06 |
| 1.0 ml 69      | +0.33 | −0.01 |
| 1.0 ml 70      | +0.41 | −0.06 |

With little effect on the initial sensitometric responses, compound 69 and 70 improved the Dmin post-processing stability 35% and 20%, respectively. The open chain azlactones function as post-processing stabilizes and thus will contribute to the overall post-processing Dmin improvement as the blocking moiety to post-processing stabilizer precursors.

What is claimed is:

1. An omega-substituted-2-propioamidoacetyl or omega-substituted-3-propioamidopropionyl compound of the formula:

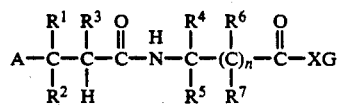

wherein

A represents a residue of a photographically useful stabilizer in which a hydrogen atom of the stabilizer selected from the group consisting of benzotriazoles, benzimidazoles, triazoles, tetrazoles, imidazoles, mercaptotetrazoles and mercaptotriazoles heterocyclics has been replaced by the remainder of the structure shown in the formula;

$R^1$, $R^2$ and $R^3$ are independently hydrogen or lower alkyl of 1 to 4 carbon atoms, with the proviso that $R^1$ can also represent a phenyl group when $R^2$ and $R^3$ are hydrogen;

$R^4$ and $R^5$ independently represent an alkyl group of 1 to 14 carbon atoms, a cycloalkyl group of 3 to 12 carbon atoms, a phenyl group or $R^1$ and $R^2$ taken together with the carbon atom to which they are joined form a carbocyclic ring of 4 to 12 ring atoms;

$R^6$ and $R^7$ independently are hydrogen or methyl;

n is 0 or 1;

X represents an oxygen, nitrogen or sulfur atom, or NH or NR where R is an alkyl or phenyl group; and G represents an organic ballasting group selected from the class consisting of alkyl, cycloalkyl, aryl, alkaryl and polymeric groups.

2. An omega-substituted-2-propioamidoacetyl or omega-substituted-3-propioamidopropionyl compound of the formula:

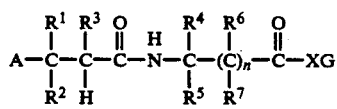

wherein

A represents a residue of a photographically useful stabilizer in which a hydrogen atom of the stabilizer selected from the group consisting of benzotriazoles, benzimidazoles, triazoles, tetrazoles, imidazoles, mercaptotetrazoles, and mercaptotriazoles has been replaced by the remainder of the structure shown in the formula;

$R^1$, $R^2$ and $R^3$ are independently hydrogen or lower alkyl of 1 to 4 carbon atoms, with the proviso that $R^1$ can also represent a phenyl group when $R^2$ and $R^3$ are hydrogen;

$R^4$ and $R^5$ independently represent an alkyl group of 1 to 14 carbon atoms, a cycloalkyl group of 3 to 12 carbon atoms, or $R^1$ and $R^2$ taken together with the carbon atom to which they are joined form a carbocyclic ring of 4 to 12 ring atoms;

$R^6$ and $R^7$ independently are hydrogen or methyl;

n is 0 or 1;

X represents an oxygen, nitrogen or sulfur atom, or NH or NR where R is an alkyl or phenyl group; and G represents an organic ballasting group selected from the class consisting of alkyl, cycloalkyl, aryl, alkaryl and polymeric groups.

3. The compound of claim 1 wherein $R^4$ and $R^5$ independently represent alkyl group of 1 to 14 carbon atoms or aryl group of 5 to 12 ring atoms.

4. The compound of claim 1 wherein G is selected from the group consisting of alkyl and aryl groups.

5. The compound of claim 3 wherein G is selected from the group consisting of alkyl or aryl groups.

6. The compound of claim 1 wherein G is a phenyl group.

7. The compound of claim 3 wherein G is a phenyl group.

8. The compound of claim 1 wherein G is a substantially perfluorinated alkyl group.

9. The compound of claim 3 wherein G is a substantially perfluorinated alkyl group.

10. The compound of claim 1 wherein $R^1$, $R^2$ and $R^3$ are selected from hydrogen and alkyl group and at least one of $R^1$, $R^2$ and $R^3$ is an alkyl group.

11. The compound of claim 4 wherein $R^1$, $R^2$ and $R^3$ are selected from hydrogen and alkyl group and at least one of $R^1$, $R^2$ and $R^3$ is an alkyl group.

12. The compound of claim 5 wherein $R^1$, $R^2$ and $R^3$ are selected from hydrogen and alkyl group and at least one of $R^1$, $R^2$ and $R^3$ is an alkyl group.

13. A compound of the formula

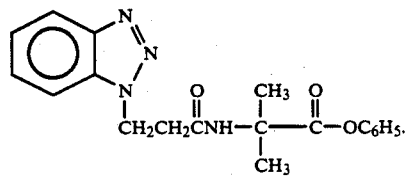

14. The compound of claim 2 wherein G is a polymeric group.

15. The compound of claim 2 wherein G is an alkyl group.

* * * * *

UNITED STATES PATENT AND TRADEMARK OFFICE
CERTIFICATE OF CORRECTION

PATENT NO. : 5,194,623
DATED : March 16, 1993
INVENTOR(S) : Krepski et al.

It is certified that error appears in the above-indentified patent and that said Letters Patent is hereby corrected as shown below:

Column 1, line 61, delete "useful" and insert --Useful--.

Column 12, line 63, delete "diglyoidly" and insert --dyglycidyl--.

Column 17, line 19, delete "$CH_2CH_2C-C-C\!-\!\!-\!C-OC_6H_5$" and insert "$CH_2CH_2C-N-C\!-\!\!-\!C-OC_6H_5$"

UNITED STATES PATENT AND TRADEMARK OFFICE
CERTIFICATE OF CORRECTION

PATENT NO. : 5,194,623
DATED : March 16, 1993
INVENTOR(S) : Krepski et al.

It is certified that error appears in the above-indentified patent and that said Letters Patent is hereby corrected as shown below:

Column 18, Example 6, delete

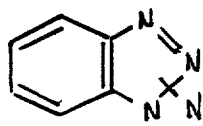

and insert

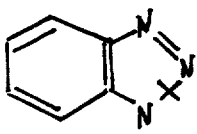

Column 19, Example 12, delete "—$OC_{16}H_{33}$"
and insert -—$OC_{16}H_{13}$--.

UNITED STATES PATENT AND TRADEMARK OFFICE
CERTIFICATE OF CORRECTION

PATENT NO. : 5,194,623
DATED : March 16, 1993
INVENTOR(S) : Krepski et al.

It is certified that error appears in the above-indentified patent and that said Letters Patent is hereby corrected as shown below:

Column 21, Example 34, delete 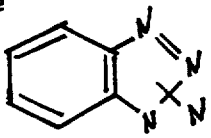

and insert 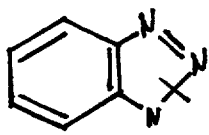

Column 21, Example 34, delete the ditto marks under column $R^3$ and insert --CH$_3$--.

Column 31, line 46, delete "isi" and insert --is--.

Signed and Sealed this

Sixth Day of September, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,194,623
DATED : March 16, 1993
INVENTOR(S) : Krepski et al.

It is certified that error appears in the above-indentified patent and that said Letters Patent is hereby corrected as shown below:

Column 12, line 63, delete "diglyoidyl" and insert --diglycidyl--.

Signed and Sealed this

Seventh Day of February, 1995

BRUCE LEHMAN

Attest:

Attesting Officer

Commissioner of Patents and Trademarks